United States Patent [19]

Steele

[11] Patent Number: 5,197,944
[45] Date of Patent: Mar. 30, 1993

[54] ANKLE CLAMP

[75] Inventor: John Steele, Germantown, Tenn.

[73] Assignee: Smith & Nephew Richards Inc., Memphis, Tenn.

[21] Appl. No.: 859,666

[22] Filed: Mar. 30, 1992

[51] Int. Cl.⁵ .............................................. A61F 5/00
[52] U.S. Cl. ......................................... 602/27; 602/36; 606/86
[58] Field of Search ................ 602/23, 26, 32, 34, 602/35, 36, 37, 38, 40; 606/86; 128/882

[56] References Cited

U.S. PATENT DOCUMENTS

| | | | |
|---|---|---|---|
| 1,928,658 | 10/1933 | Anderson | 602/38 |
| 1,939,779 | 12/1933 | Jones | 602/38 |
| 2,089,993 | 8/1937 | Carabba | 602/27 |
| 2,129,635 | 9/1938 | Anderson | 602/38 |
| 2,266,628 | 12/1941 | Finochietto | 602/36 |
| 2,446,470 | 8/1948 | Godwin | 128/882 |
| 2,494,792 | 1/1950 | Bloom | 602/37 |
| 2,706,475 | 4/1955 | Reynolds | 602/37 |
| 3,401,688 | 9/1968 | Crutchfield | 602/37 |
| 3,477,429 | 11/1969 | Sampson | 128/92 |
| 4,706,660 | 11/1987 | Petersen | 128/92 |
| 4,869,240 | 9/1989 | Boren | 602/32 |
| 5,020,797 | 6/1991 | Burns | 602/23 |

Primary Examiner—Robert A. Hafer
Assistant Examiner—Michael Brown
Attorney, Agent, or Firm—Pravel, Hewitt, Kimball & Krieger

[57] ABSTRACT

An ankle clamp apparatus for use with tibial cutting instruments has a frame with pivoting arms attached for gripping a patient's ankle during use. The arms can be held open with latches prior to placement and quickly released to grip the patient's leg by depressing the latches. The device can be operated by a surgeon using only one hand to depress the latches.

27 Claims, 3 Drawing Sheets

ANKLE CLAMP

BACKGROUND OF THE INVENTION

1. Field of the Invention

The present invention relates to orthopedic instrumentation and more particularly relates to an ankle clamp apparatus which allows a surgeon to use one hand to attach the ankle clamp as part of an overall tibial alignment assembly. More particularly, the present invention relates to an improved ankle clamp apparatus with a locking feature that secures movable arm portions of the clamp in an open position until the clamp is positioned for use at which time the locking feature may be disengaged from the arms, allowing the clamp to tighten around the ankle of the patient.

2. General Background

During total knee replacement, the upper or proximal portion of the tibia is cut away using a saw such as a reciprocal saw. The surgeon places the saw on the top of a cutting block that is positioned at the proximal end of the tibia. The cutting block provides a surface that supports the saw blade in a desired, steady position. Placement of tibia instrumentation and cutting block is critical because the block must be positioned correctly and held firm during the entire cutting operation so that an accurate cut is made.

One way to mount the cutting block and its associated instrumentation is to actually mount the cutting block to an intermedullary canal, that occupies the hollowed inside portion of the tibia, so that the cutting block lies adjacent to the bone to be sawed.

A second way to correctly align the cutting block is through an external or extramedullary alignment assembly. These devices include extendable telescoping, or solid rod assemblies with a lower end portion carrying an ankle clamp that grasps the patient's ankle. By holding the patient's leg externally and very firmly with assist from the ankle clamp, the cutting block can be positioned and held steady during the cutting so that the cuts are made precisely by the surgeon.

Extramedullary alignment assemblies include the extendable telescoping rod for the purpose of adjusting the entire instrumentation assembly to the length of a particular patient's leg. Similarly, extramedullary alignment assemblies which include a solid non-extendable rod permit the cutting block to slide thereon and be selectively positioned to a desired clamping location. Additionally, lateral adjustments are available for moving the extramedullary alignment assembly away from or toward the patient's tibia.

Presently, ankle clamps are commercially available which include a frame (also known as a "Y-block") with a pair of arms pivotally attached to the frame on opposite sides. These arms are spring loaded so that they are biased to a closed clamping position until opened by the surgeon. These prior art clamps do not provide a means to maintain the arms in an open position, and because there are two arms, two hands are required to open these prior art type ankle clamps.

SUMMARY OF THE PRESENT INVENTION

The present invention provides an improved ankle clamp with a locking mechanism that allows a surgeon to use one hand to attach the ankle clamp for a tibial alignment assembly. The present invention uses a mechanism that locks the arms of the clamp in an open position until the clamp is positioned by the surgeon at the patient's ankle. The surgeon can then unlock the arms simultaneously by depressing release latches so that the clamp tightens quickly around the ankle.

The apparatus includes an ankle clamp frame, preferably in the form of a Y-block having a pair of angularly intersecting side portions with a gap there between that accepts the patient's ankle during use.

A pair of pivots are provided at the ends of the pair of intersection portions of the frame. Each of the pivots form an attachment position for the movable arms. An arm is attached to each of the spaced apart sides of the Y-block frame at the pivots. The arms are movable between open and closed positions and are biased with springs to assume the closed position which grips the patient's ankle during use.

Each of the arms includes a free end portion spaced from its pivot, and a notched end portion adjacent the arm pivot. During operation, each arm is rotated toward an open position, tightening its helical spring. The spring is pivotally attached to the arm. The free end of the spring is attached to the latch. Once the arm is rotated beyond full open, a notched geometry on the arm is exposed into which the latch seats. The notches cooperate with the latches to secure the arms in open position. Each of the latches has an externally positioned pressure plate surface that can be manually depressed for releasing the latch from the respective movable arm.

With the clamp in the open position, the surgeon positions the clamp on the ankle. Next, the surgeon squeezes the latches which move clear of the notch thus allowing the arms to close. The apparatus as described allows the surgeon to use one hand to attach the ankle clamp for a tibial alignment assembly, simplifying the overall tibial cutting surgical procedure.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein.

DETAILED DESCRIPTION OF THE PREFERRED EMBODIMENT

Figure 1:
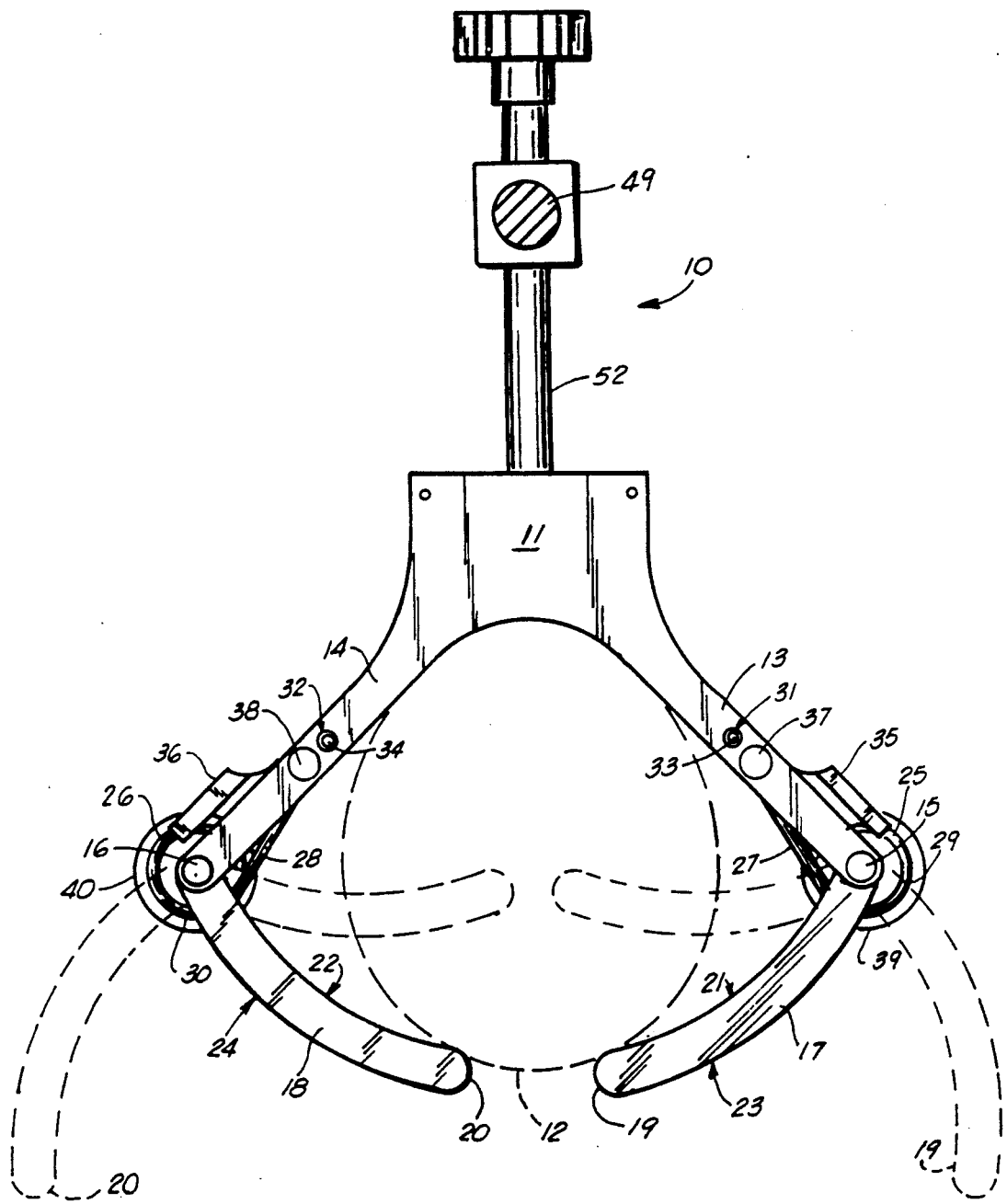
FIG. 1 is a plan view of the preferred embodiment of the apparatus of the present invention.
Figure 2:
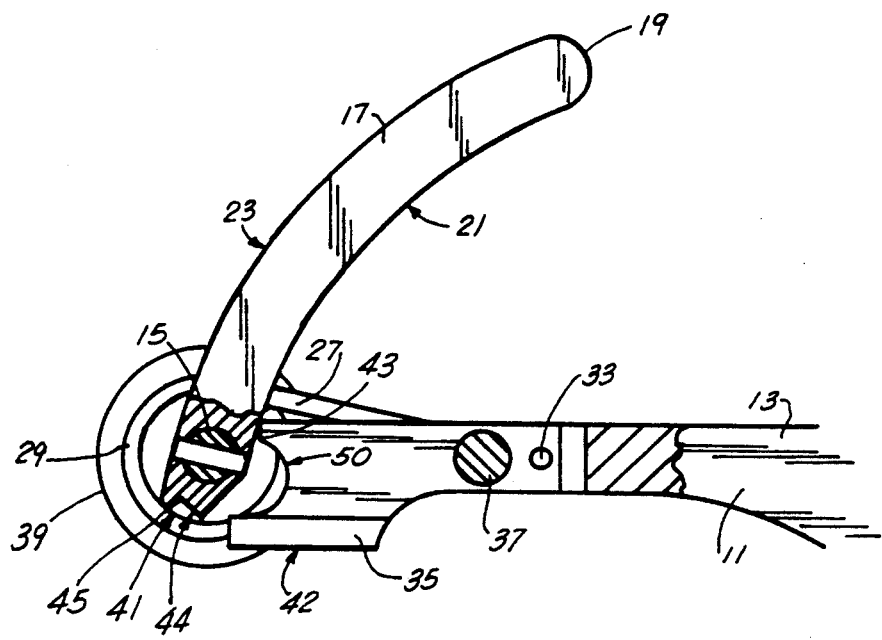
FIG. 2 is a fragmentary plan view of the preferred embodiment of the apparatus of the present invention illustrating the clamp arm in closed position.
Figure 3:
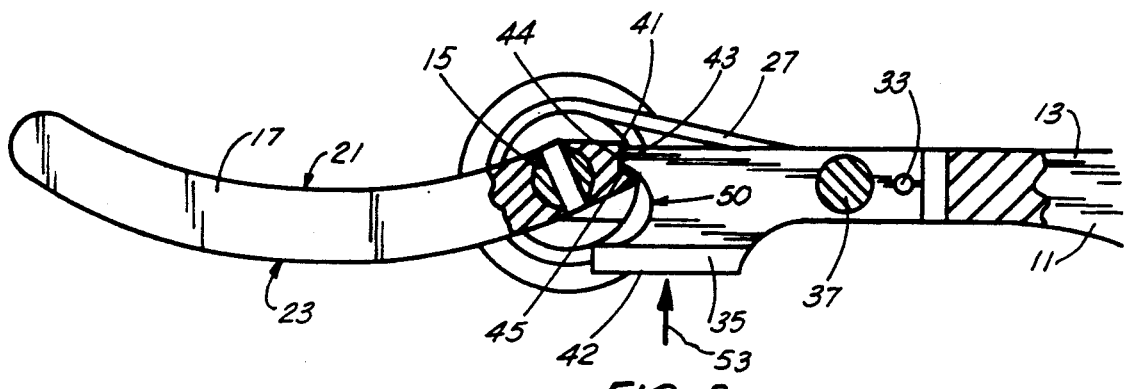
FIG. 3 is a fragmentary plan view of the preferred embodiment of the apparatus of the present invention illustrating the arm in open position.
Figures 4, 5:
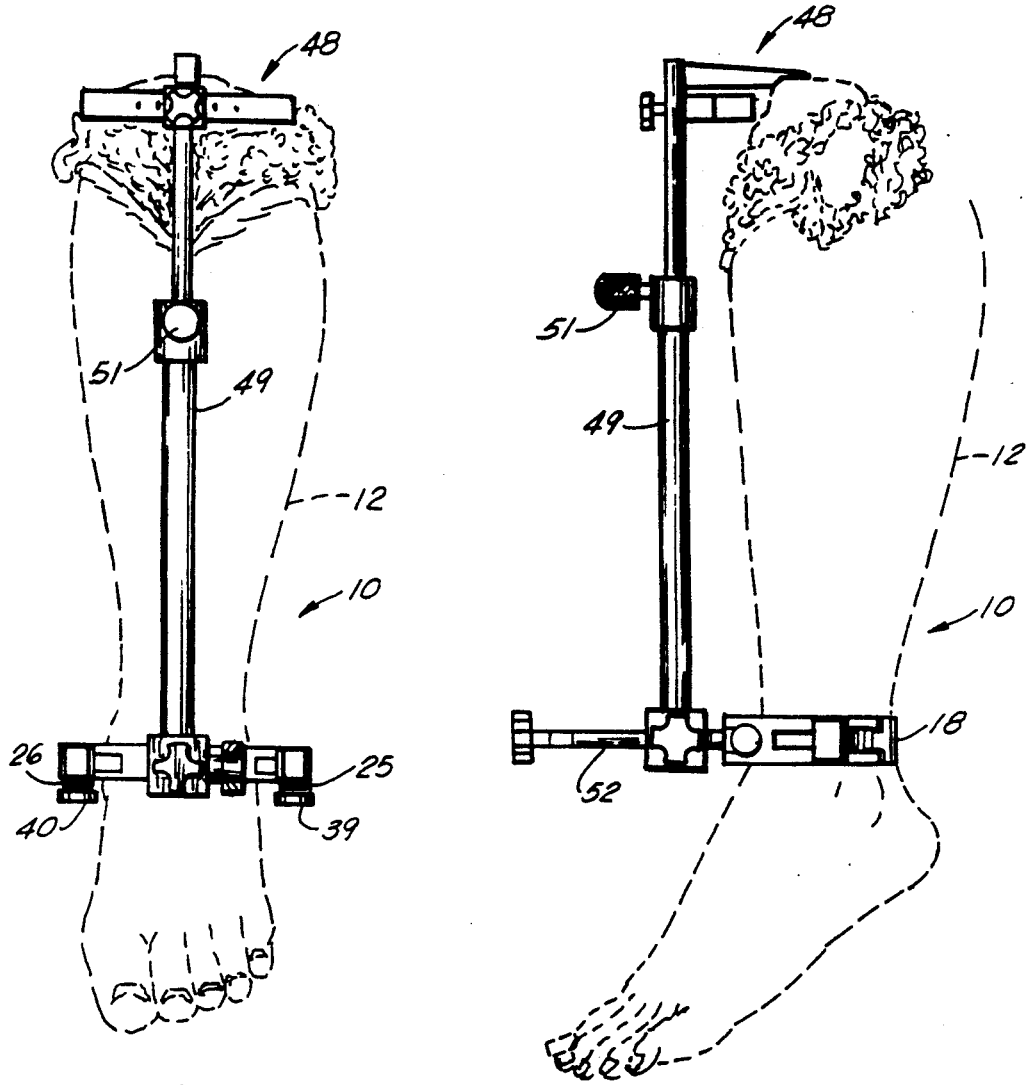
FIG. 4 is a front schematic elevational view of the preferred embodiment of the apparatus of the present invention illustrating its attachment to a patient's leg and ankle.
FIG. 5 is a side elevational schematic view of the preferred embodiment of the apparatus of the present invention illustrating its position during use with regard to the patient's leg and ankle.

FIGS. 1-6 illustrate the preferred embodiment of the apparatus of the present invention designated generally by the numeral 10. Ankle clamp apparatus 10 includes a frame 11 preferably in the shape of a Y-block as shown in FIG. 1. The frame 11 provides an open recess between a pair of fixed appendages 13, 14. The recess accommodates a patient's leg 12 at the ankle area as shown in FIGS. 1, 4 and 5 when the ankle clamp 10 is in closed position as shown in hard lines in FIGS. 1 and 5. Fixed appendages 13, 14 are angularly oriented with respect to each other, by a measure of approximately ninety degrees (90°). Each fixed appendage 13, 14 provides a pivot 15, 16 respectively that pivotally supports movable arms 17, 18 respectively.

Each arm 17, 18 provides respective free end portions 19, 20, and is preferably curved having outer concave surfaces 21, 22 and inner convex surfaces 23, 24 respectively. A pair of coil springs 25, 26 bias each of the arms 17, 18 into the closed position shown in hard lines in FIG. 1.

Figure 6:
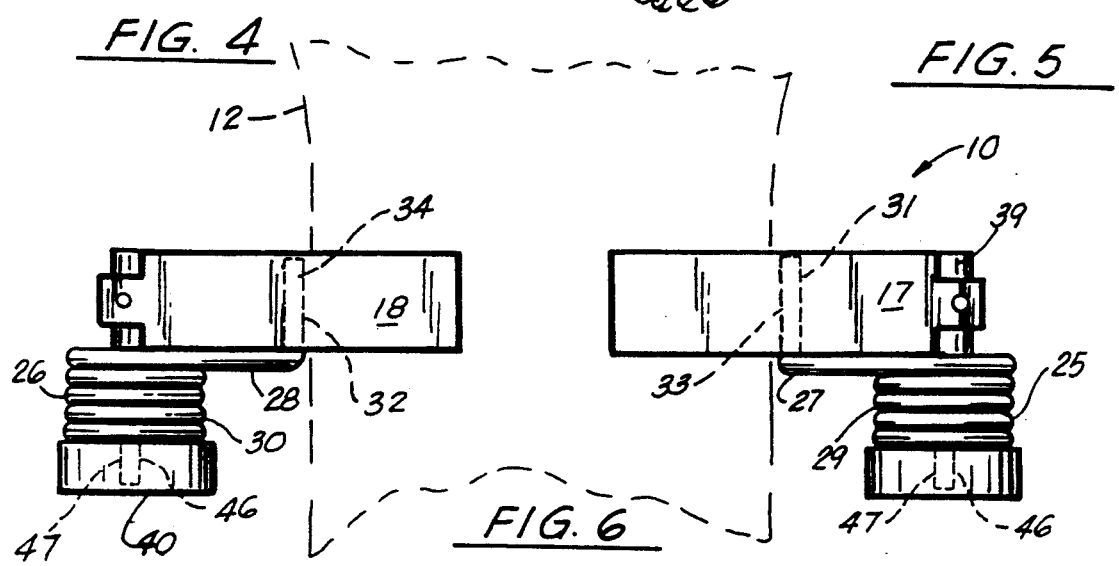
FIG. 6 is a fragmentary elevational view illustrating the arms in closed position about a patient's ankle.

Springs 25, 26 each have straight portions 27, 28, coiled portions 29, 30, and each coil spring 25, 26 has a spring anchor 47 which fits into a spring peg opening 46 in each spring peg 39, 40 (see FIG. 6). The straight portions 27, 28 of springs 25, 26 having spring attachments 33, 34 respectively that register in spring attachment openings 31, 32. Openings 31, 32 are cylindrical openings having an internal diameter slightly larger than the external diameter of spring attachments 33, 34.

A pair of latches 35, 36 are provided respectively upon the fixed appendages 13, 14. Latches 35, 36 are used to secure its respective arm 17, 18 in the open position (see FIG. 3). The coil springs 25, 26 fit around spring pegs 39, 40 respectively which are mounted at the free ends of fixed appendages 13, 14 as shown in FIG. 1. Each latch 35, 36 has an opening about the same diameter as its associated spring attachment. The spring attachments 33, 34 pass through the opening in each respective latch 35, 36 and through the larger openings 31, 32. This allows a small amount of travel of each spring attachment 33, 34 in the openings 31, 32. Because the openings in each latch 35, 36 are about the same size as the spring attachments 33, 34, the latches 35, 36 are urged by the springs 25, 26 to move to the latching position of FIG. 3. Each spring attachment 33, 34 moves in its opening 31, 32 toward the recess between appendages 13, 14 causing each latch 35, 36 to pivot about its pivot 37, 38 and rotating free end 43 away from the recess area between appendages 13, 14 (i.e. latching position).

FIGS. 2 and 3 show a single fixed appendage 13 and its associated movable arm 17 for purposes of illustrating the operation of a latch 35 with regard to the movement of arm 17 between closed (FIG. 2) and open (FIG. 3) positions.

In FIG. 2, the latch 35 provides a latch free end 43 that communicates with latch pressure plate 42, both spaced away from the pivot 37. The pressure plate 42 is depressed by the surgeon in order to release the arm 17 so that it moves from the open position of FIG. 3 to the closed position of FIG. 2. The position of arm 17 in FIG. 2 is achieved if the device is moved to the closed position when a patient's ankle is not being gripped. Otherwise, the patient's leg 12 forms a stop for receiving the moving arms 17, 18 as shown in FIG. 1. In FIG. 1, the full open position as well as the full closed position of the arms is shown in phantom lines, with the actual operative gripping position about a patient's leg 12 being shown in hard lines for arm 17.

Arm 17 provides a recess or notch 41 receptive of latch free end 43 as shown in FIG. 3. The notch 41 is comprised of a pair of angularly intersection flat notch surfaces 44, 45 which are angled approximately ninety degrees (90°) with respect to each other. During use, the surgeon pulls arms 17 and 18 from the closed position of FIG. 2 into the open position of FIG. 3. In so doing, the latch free end 43 registers with the notch 41 and abuts the surface 44 as shown in FIG. 3. At this time, the surgeon releases the arm 17 or 18 and coil spring 25 or 26 holds the surface 44 tightly against the surface 43 in attempting to close the arm 17. However, the latch 35 free end 43 engages the surface 44 and prevents the arm 17 from moving toward the closed position of FIG. 2.

In order to move the arms 17, 18 into the closed position of FIG. 2, the surgeon presses against the pressure plate 42 rotating the latches 35, 36 in the direction of arrow 53 in FIG. 3, thus rotating the latch 35 about its pivot 37. This movement of the latch 35 about its pivot 37 disengages the surface 43 from the surface 44 and places the notch 41 adjacent the concave surface 50 portion of latch 35 which allows the arm 17 or 18 to freely pivot toward the closed position of FIG. 2. The arm 17 concave surface 21 eventually engages the latch free end 43 as shown in FIG. 2 which defines the innermost possible position of the pivoting arms 17, 18.

In FIGS. 1, 2, and 3, ankle clamp 10 is shown as part of an overall tibial instrumentation assembly that includes tibial cutting block assembly 48 and telescoping rod assembly 49.

The following Table 1 lists the part numbers and part descriptions as used herein and in the drawings attached hereto.

TABLE 1

PARTS LIST

| PART NUMBER | PART DESCRIPTION |
| --- | --- |
| 10 | ankle clamp apparatus |
| 11 | frame |
| 12 | patient's leg |
| 13 | fixed appendage |
| 14 | fixed appendage |
| 15 | pivot |
| 16 | pivot |
| 17 | arm |
| 18 | arm |
| 19 | free end |
| 20 | free end |
| 21 | concave surface |
| 22 | concave surface |
| 23 | convex surface |
| 24 | convex surface |
| 25 | spring |
| 26 | spring |
| 27 | straight portion |
| 28 | straight portion |
| 29 | coiled portion |
| 30 | coiled portion |
| 31 | spring attachment opening |
| 32 | spring attachment opening |
| 33 | spring attachment |
| 34 | spring attachment |
| 35 | latch |
| 36 | latch |
| 37 | latch pivot |
| 38 | latch pivot |
| 39 | spring peg |
| 40 | spring peg |
| 41 | notch |
| 42 | latch pressure plate |
| 43 | latch free end |
| 44 | notch surface |
| 45 | notch surface |
| 46 | spring peg opening |
| 47 | spring anchor |
| 48 | tibial cutting block assembly |
| 49 | telescoping rod assembly |
| 50 | concave surface |

TABLE 1-continued

PARTS LIST

| PART NUMBER | PART DESCRIPTION |
|---|---|
| 51 | vertical adjustment bolt |
| 52 | threaded connection |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An ankle clamp for supporting tibial cutting instruments, comprising:
  a) an ankle clamp frame comprising a pair of angularly intersecting fixed appendage portions with a gap therebetween that accepts a patient's ankle during use, and an elongated rod with upper and lower end portions and the rod attaching at its lower end portion to the fixed appendage portions at a position therebetween;
  b) a pair of pivots mounted on the frame and respectively at the free end of each fixed appendage portion;
  c) a pair of movable arms, each with an outer free end portion and an inner attachment end portion, and the arms are pivotally attached respectively to the free end of the fixed appendage portions at said pivots, and movably between open and closed positions, the frame and arms defining an assembly during use;
  d) latch means carried by the assembly of the frame and the attached arms for holding the arms in the open position;
  e) the latch means including spring loaded quick release means for moving a selected arm to the closed position; and
  f) tibial cutting block assembly positioned during use at the upper end portion of the rod, for providing an alignment guide during cutting of the tube.

2. The apparatus of claim 1 wherein the frame includes a yoke that is generally Y-shaped.

3. The apparatus of claim 1 wherein the latch means includes springs carried by the frame at a position adjacent the pivot.

4. An ankle clamp for supporting tibial cutting instruments, comprising:
  a) an ankle clamp frame comprising a pair of angularly intersecting fixed appendage portions with a gap therebetween that accepts a patient's ankle during use, and an elongated rod with upper and lower end portions and the rod attaching at its lower end portion to the fixed appendage portions at a position therebetween;
  b) a pair of pivots mounted on the frame and respectively at the free end of each fixed appendage portion;
  c) a pair of movable arms, each with an outer free end portion and an inner attachment end portion, and the arms are pivotally attached respectively to the free end of the fixed appendage portions at said pivots, and movably between open and closed positions, the frame and arms defining an assembly during use;
  d) latch means carried by the assembly of the frame and the attached arms for holding the arms in the open position;
  e) the latch means including quick release means for moving a selected arm to the closed position;
  f) tibial cutting block assembly positioned during use at the upper end portion of the rod, for providing an alignment guide during cutting of the tube;
  g) means for biasing the movable arms to the closed position, and;
  h) wherein the biasing means includes spring means carried by the frame for urging the arms to move to the closed position.

5. The apparatus of claim 1 wherein each arm has a notched end portion at its inner attachment end portion.

6. The apparatus of claim 5 wherein the latch means engages the notched end portion when the arms are in the open position.

7. The apparatus of claim 1 wherein the frame includes a yoke with a pair of integrally connected fixed arms that are angularly oriented, and an open recess is provided between the fixed arms the open recess being receptive of the patient's ankle during use.

8. An ankle clamp for supporting tibial cutting instruments, comprising:
  a) an ankle clamp frame comprising left and right laterally extending fixed appendage portions with a gap therebetween, the appendages defining a plane, and an elongated rod that connects to the fixed appendages and extends away from the plane of the appendages;
  b) a pair of arms, each attached to one of the pair of fixed appendage portions and movable between open and closed positions, and each arm biased to assume the closed position;
  c) latch means for holding the arms in the open position;
  d) release means carried by the frame for moving a selected arm to the closed position; and
  e) a tibial cutting assembly supported at the upper end of the rod.

9. The apparatus of claim 8 wherein the frame includes a yoke that is generally Y-shaped.

10. The apparatus of claim 8 wherein each side portion is a fixed arm having a free end, and the arms are positioned at the free ends of the fixed arms.

11. The apparatus of claim 8 wherein the release means is carried by the frame.

12. The apparatus of claim 8 where the latch means is capable of engaging a portion of the arm adjacent the attachment of the arm to the frame.

13. The apparatus of claim 12 wherein each of the arms is notched at one end portion, and the latch means comprises a latch member mounted respectively on each of the fixed appendage portions of the frame, the latch members engaging the notches when the arms are in the open position.

14. The apparatus of claim 13 wherein the latch members are pivotally mounted to the frame.

15. The apparatus of claim 8 wherein each arm has a notched end portion opposite its free end portion.

16. The apparatus of claim 15 wherein the latch means has means for engaging the notched end portion when the arms are in the open position.

17. The apparatus of claim 8 wherein there is further included a spring for moving the movable arms to the closed position.

18. The apparatus of claim 17 wherein the spring includes coil springs for urging the arms to move to the closed position.

19. The apparatus of claim 18 wherein there are a pair of coil springs carried respectively on each of the fixed appendage portions of the frame.

20. The apparatus of claim 17 wherein the frame includes a yoke with a pair of integrally connected fixed arms that are angularly oriented, and an open recess is provided between the fixed arms that is receptive of the patients ankle during use.

21. The apparatus of claim 20 wherein each movable arm is an elongated generally curved member.

22. The apparatus of claim 17 wherein there is further provided a spring peg mounted at the free end of each frame fixed appendage portion, and the spring is supported upon each spring peg.

23. The apparatus of claim 22 wherein each spring is anchored at one end portion to the spring peg and at its other end portion to a frame fixed appendage portion.

24. The apparatus of claim 23 wherein the latch means are latches that are movable between latching and unlatching positions.

25. The apparatus of claim 24 wherein the latches are biased to assume the latching position.

26. The apparatus of claim 25 wherein the springs bias each latch to the latching position.

27. The apparatus of claim 8 wherein the quick release means comprises in part a pair of locking members mounted respectively on the sides of the frame.

* * * * *